United States Patent [19]
Sem-Jacobsen

[11] 3,954,100
[45] May 4, 1976

[54] FLEXIBLE SENSOR PAD FOR NON-ATTACHED MONITORING EKG SIGNALS OF HUMAN SUBJECTS

[75] Inventor: Carl Wilhelm Sem-Jacobsen, Oslo, Norway

[73] Assignee: International Defense Consultant Services, Inc., Washington, D.C. ; a part interest

[22] Filed: Dec. 10, 1974

[21] Appl. No.: 531,329

[52] U.S. Cl. .................. 128/2.06 E; 128/DIG. 4
[51] Int. Cl.² .......................................... A61B 5/04
[58] Field of Search ............ 128/2.06 E, 2.1 E, 404, 128/416–418, DIG. 4

[56] References Cited
UNITED STATES PATENTS

| | | | |
|---|---|---|---|
| 1,212,541 | 1/1917 | Morse | 128/417 |
| 2,943,628 | 7/1960 | Howell | 128/418 |
| 3,187,745 | 6/1965 | Baum et al. | 128/2.06 E |
| 3,386,445 | 6/1968 | McDonald | 128/417 |
| 3,498,291 | 3/1970 | Bunn | 128/2.06 E |
| 3,542,010 | 11/1970 | Love | 128/2.1 E |
| 3,581,736 | 6/1971 | Zenkich | 128/2.06 E |
| 3,720,209 | 3/1973 | Bolduc | 128/2.06 E |
| 3,817,252 | 6/1974 | Maurer | 128/417 |
| 3,888,240 | 6/1975 | Reinhold, Jr. et al. | 128/2.06 |

FOREIGN PATENTS OR APPLICATIONS
274,612    7/1951    Switzerland .................... 128/DIG. 4

OTHER PUBLICATIONS
Schaudinischky et al., "Shape Conforming Electrode," Med. & Biol. Eng., Vol. 7, pp. 341–343, Permagon Press, 1969.

*Primary Examiner*—Robert W. Michell
*Assistant Examiner*—Lee S. Cohen
*Attorney, Agent, or Firm*—Mason, Fenwick & Lawrence

[57] ABSTRACT

A flexible sensor pad upon which a subject sits or lies for acquiring electrocardiogram (EKG) signals from a human subject for continuous monitoring of the subject without attachments to the subject, as during piloting of aircraft or during transportation on a stretcher, to enable activation of an alarm upon certain conditions. The sensor pad includes a flexible waterproof backing sheet of textile fabric, a pair of flexible pick-up panels of non-corrosive, highly conductive fabric such as cloth formed of threads having metallic strands, and a thin cover cloth which is permeable to peripheral perspiration of the subject to effect transmission of the EKG signals to the pick-up panels by the perspiration.

10 Claims, 6 Drawing Figures

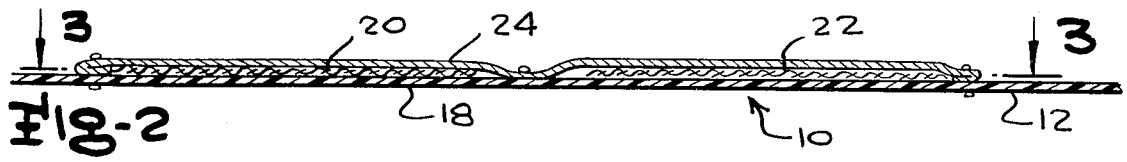
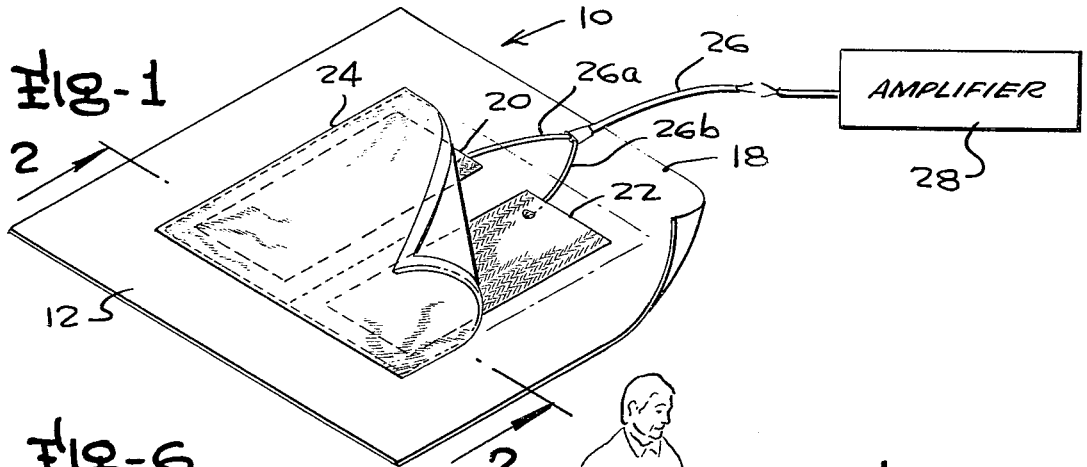
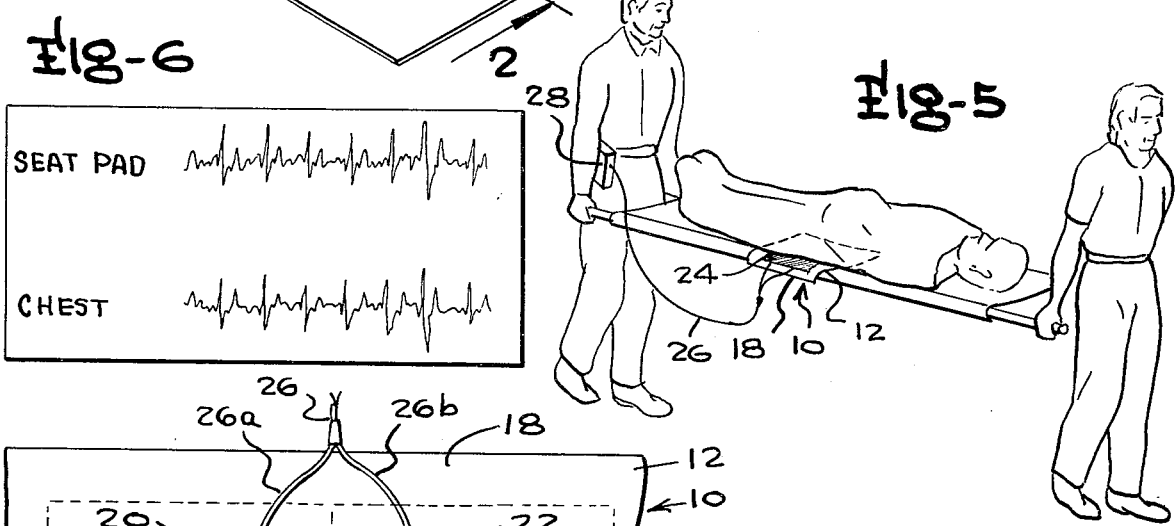
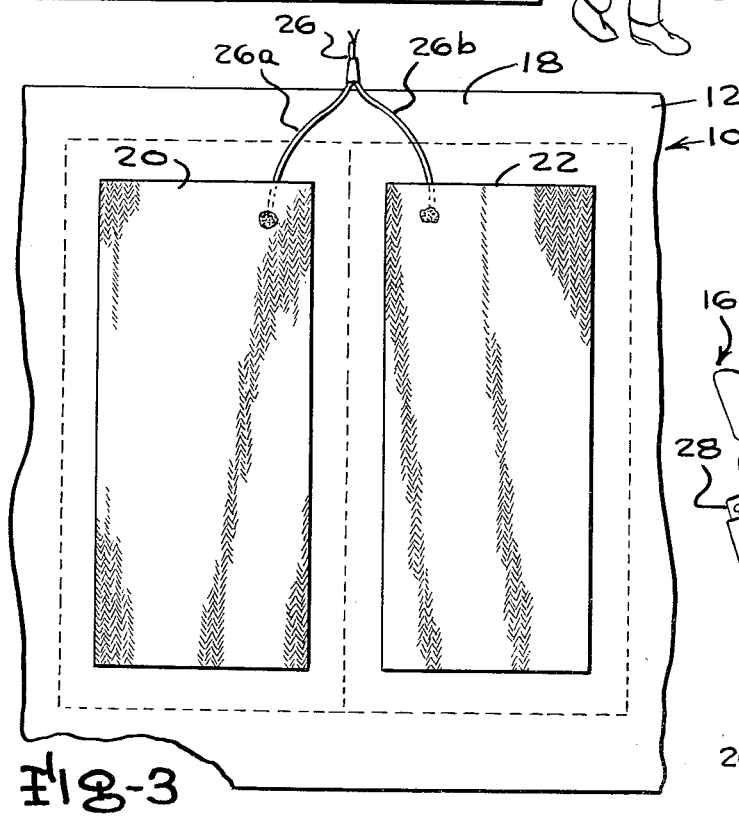
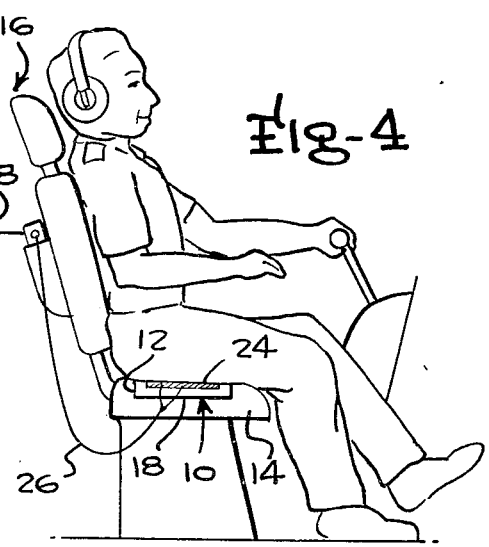

FLEXIBLE SENSOR PAD FOR NON-ATTACHED MONITORING EKG SIGNALS OF HUMAN SUBJECTS

BACKGROUND AND OBJECTS OF THE INVENTION

The present invention relates in general to sensor devices for biomedical monitoring of electrocardiogram or EKG signals from human subjects without attachment to the subjects of any leads or sensor devices, and more particularly to sensor devices constructed in pad form on which a human subject may sit or on which a part of the body of the human subject may rest which requires no power source but is capable of obtaining EKG signals from the subject transmitted to the sensor device through the medium of the subject's perspiration to provide EKG signals appropriate for monitoring the subject's heart action, especially usable to record EKG signals or sense EKG signals in such way that sudden serious heart failure of persons such as aircraft pilots can be immediately recognized and an alarm generated.

Intermittently, pilots in command of aircraft are struck with incapacitation due to pain, heart failure, seizure or other medical disorders. In almost all cases except for sudden seizure and sudden heart failure, the pilot has time to request assistance from the co-pilot or other aircraft personnel and ask the co-pilot to take over. In attacks of sudden serious heart failure, the pilot is not capable ordinarily of warning the co-pilot due to the way he loses consciousness.

With the increasing number and age of airline pilots, inadvertently some of them have died of heart failure while on active duty in the cockpit. Over the past years, incidents of sudden incapacitation due to heart failure among aircraft pilots actually flying planes have increased. With the increase in number and the advancing age of the commercial airline pilot population, this increase was to be expected. Over the past ten years or so, at least three pilots a year have met sudden incapacitation due to coronary heart failure and death while in command of passenger-carrying commercial aircraft. It is believed that about fifteen pilots have died from sudden heart failure while in charge of a commercial airliner in the final phase of the landing procedure. It is during the final phase of the landing procedure when the co-pilot is most busy with radio communication, notes, checklists, and other tasks and therefore least likely to be instantly aware of the pilot's difficulty. During such landing approaches with modern jet aircraft, the five to fifteen seconds which might pass before the co-pilot realizes the situation and can take over is often such that it is then too late for him to be effective.

To combat these serious problems, it is desirable to have means by which the EKG of the pilot may be continuously monitored so that electronic instruments receiving the EKG signals may sense when pilot heart failure may be occurring and alert the co-pilot by an alarm so that he will be prepared to take over in the event of sudden heart failure and instant incapacitation of the pilot. Since it is impractical in airline operations, and often impossible, to attach leads to the pilot for biomedical monitoring such as monitoring the EKG of the pilot, it is desirable to develop suitable ways to obtain such biomedical signals from the pilot so as to provide a good quality EKG from the pilot with no immediate preflight preparation of the pilot and without attachment of any special electrodes or sensors of any type to the pilot's body. Also it is important to avoid electrical leads or connections to any part of the pilot's wearing apparel such as might restrict or interfere with the pilot's mobility, performance and/or comfort.

Also, it is desirable in other situations to be able to monitor the EKG of a human subject in other circumstances without having to attach any sensors or monitoring devices to the body or clothing of the subject. For example, it is highly desirable in many cases to be able to monitor the EKG signals of a patient being transported on a stretcher or under similar circumstances where connections to fixed heart monitoring installations may not be readily accessible to provide an alarm or record of the subject's EKG during transportation of the subject.

An object of the present invention, therefore, is the provision of a novel sensor device in pad form for obtaining EKG signals from human subjects without attachment of any leads or devices to the body or clothing of the subject, whereby EKG signals from the patient can be monitored simply when a part of the patient's body is resting upon the sensor device.

Another object of the present invention is the provision of a novel EKG monitoring sensor in pad form having a pair of highly conductive flexible metallic panels arranged on a non-conductive waterproof sheet or carrier, adapted to obtain EKG signals transmitted by the subject through the medium of the subject's perspiration to the sensor device when the subject is seated upon the pad or a portion of the subject's body is resting upon the pad.

Other objects, advantages and capabilities of the present invention will become apparent from the following detailed description, taken in conjunction with the accompanying drawings illustrating a preferred embodiment of the invention.

BRIEF DESCRIPTION OF THE FIGURES

FIG. 1 is a perspective view of the EKG monitoring sensor device of the present invention constructed in pad form, shown as connected to a signal amplifier and having parts of the pad broken away to illustrate inner components of the pad construction;

FIG. 2 is a vertical section view through the EKG sensor pad, taken along the line 2—2 of FIG. 1;

FIG. 3 is a horizontal section view of the sensor pad, taken along the line 3—3 of FIG. 2 to show the pad with the overlying porous fabric cover removed;

FIG. 4 illustrates the use of the sensor pad as a commercial airline pilot's seat pad;

FIG. 5 illustrates the use of the sensor pad for monitoring EKG signals of a patient being transported on a stretcher; and FIG. 6 is a reproduction of waveforms of EKG signals obtained from the seat pad sensor of the present invention and from standard chest leads of a patient showing a comparison of EKG signals from these two sources.

DETAILED DESCRIPTION OF A PREFERRED EMBODIMENT

Referring to the drawings, wherein like reference characters designate corresponding parts throughout the several figures, the non-body-attached EKG sensor device of the present invention is indicated generally by the reference character 10 and is described in one embodiment suitable for use as a seat pad for the pilot's seat, or for both the pilot and co-pilot seats, of commercial aircraft, or for use as a single pad or a plurality of pads disposed on a stretcher underlying a patient being carried on the stretcher. In the case of the use of the EKG sensor seat pad, the EKG signals are picked up by the seat pad through the pilot's pants when he is in his seat in the cockpit with fastened seatbelt, by transmission of the EKG signals from the pilot's body to the seat pad through the perspiration of the pilot which acts as the conductive medium. It will be understood that suitable amplifier circuitry connected to the seat pad will amplify the EKG signals and the amplified EKG signals may be applied to suitable circuitry to trigger a warning device when the EKG data is outside an acceptable envelope or otherwise indicates an abnormal heart condition to activate an audible alarm and/or visible alarm signifying to the co-pilot, and as desired to other crew members, the necessity for prompt corrective action. Similarly, a miniaturized amplifier will be connected to the sensor pad employed on stretchers or similar conveyances for prone human bodies to be monitored, to supply amplified EKG signals to detecting circuitry which detects abnormal EKG signals and activates the desired alarm. These two suggested applications, which are but a few of many applications for the EKG sensor pad, are illustrated in FIGS. 4 and 5.

Referring more particularly to FIGS. 1, 2, and 3, the EKG sensor pad may be in the form of a generally rectangular pad indicated at 12, of suitable size to form a seat pad which may be loosely secured to the seat portion 14 of the pilot's seat 16 of a commercial aircraft, as illustrated in FIG. 4. The rectangular seat pad 12 comprises a backing panel sheet 18 of generally rectangular configuration formed of a non-conductive, waterproof sheet of textile material which may, for example, be upholstering material or furniture covering fabric having an appearance similar to the upholstery or covering fabric of conventional aircraft seats and the like. The waterproof backing panel sheet 18 is preferably of an outline suitable for it to fit properly over the seat portion of the pilot's seat, and is preferably approximately coextensive with the normal configuration of the upwardly facing surface of the seat portion of conventional pilot's seats for commercial airliners. Superposed over the non-conductive, waterproof backing panel sheet are two strips or small panels 20 and 22 of high conductive, non-corrosive, flexible sheet material, such as two strips or panels of gold cloth or cloth formed of other metallic thread, of good electrically conductive characteristics, which are spaced from each other in electrically isolated relation and serve as pick-up sensors. The two metallic cloth panels 20 and 22 are preferably located one under each buttocks cheek or at each side of the sitting area where the pressure from the pilot's body consistently is the highest. Covering the area occupied by the two metallic cloth panels 20 and 22 and the space therebetween and a small bordering region surrounding the panels is a protective sheet 24 of thin cloth, stitched or otherwise secured about its periphery to the underlying waterproof backing panel sheet 18.

The two conductive or metallic fabric panels 20, 22, serve as the pick-up electrodes receiving the EKG signals from the pilot transmitted through the pilot's pants and the thin porous covering cloth 24 through the medium of the pilot's perspiration. Due to the normal peripheral water loss or perspiration of the pilot, a good quality EKG signal is obtained when the conductive fabric panels or strips are disposed on top of a non-conductive waterproof sheet to retain sufficient peripheral perspiration from the pilot in order to obtain adequate electrical conductivity to operate the sensor. Since there may occur rare instances where the peripheral perspiration may bead, which might prevent proper operation of the sensor, the possibility of beading is prevented by spraying the panels or strips with a conventional, known antistatic preparation or anti-static aerosol.

Two electrical lead portions 26a, 26b of a two-conductor lead 26 are secured in good electrical contact with the metallic thread or conductive components of the conductive fabric panels 20 and 22, as by soldering or otherwise securing the electrical conductive cores of the leads 26a, 26b to the panels 20 and 22 beneath the porous fabric cover 24. The two-conductor cable 26 leads to a suitable preamplifier, indicated generally at 28, such as conventional amplifiers heretofore developed for biomedical monitoring and biological amplifying applications providing amplifications for example, up to 1:2000 and having the frequency response adjusted to maximum conformance with EKG signals. The amplified EKG signals can be processed by conventional electronic equipment to detect when they depart from selected acceptable patterns or envelopes and activate alarm devices, such as audible or visible alarms to immediately signify to the co-pilot or other crew members the necessity of taking over operation from the pilot. Also, the equipment detecting the abnormal EKG signals may be transponded to ground control at nearby airports to alert the tower to sudden problems during landing and takeoff.

The seat pad type EKG sensor device may also be used to record EKG signals during operation of the aircraft by the pilot with amplification modulation equipment of types heretofore used for monitoring and recording biomedical characteristics of pilots and astronauts. Amplification modulation equipment is available which can record EKG signals as low as 5 microvolts with an input impedance of more than 20K ohms without significant background noise level.

By use of such a seat pad EKG sensor device, the whole EKG sensor and preamplifier system can be contained in the seat cushion of a pilot's seat with only one cable connection to the pilot's seat for electrical power supply to the preamplifier and for triggering the alarm which may be located, for example, on the aircraft instrument panel. No special flying suit or attachment of electrodes or cable to the body of the pilot or his clothing is necessary. Therefore there is no interference with the pilot's mobility, performance and comfort, and the pilot automatically becomes coupled with the EKG sensing system when he occupies his seat and fastens the seatbelt. The effectiveness of the seat pad type EKG sensor herein described has been proven by actual tests recording the EKG signals picked up by the seat pad sensor in comparison with EKG signals picked up by a conventional chest lead from the same sitting subject simultaneously, electrocardiogram traces from the two sources being illustrated in FIG. 6 and appropriately labeled.

An EKG signal sensor pad of the type herein described is also suitable to be located on the body-supporting surface of a stretcher, for example as illustrated in FIG. 5, against a body portion such as the seat portion, the back portion back of the shoulder blades, or the back of the legs, of a patient lying on the stretcher during transportation, to provide continuous monitoring of the EKG signals from the patient and generate an audible or visible alarm in the event of abnormal EKG signals to immediately bring this condition to the attention of the attendants.

Good initial signal pick-up from the pilot (or other body to be monitored) when the pilot first sits (or the body is deposited) on the sensor pad may be facilitated by interposing a moist pad of cotton or other material between the backing panel sheet 18 and the metallic cloth panels 20, 22.

While but one preferred embodiment of the present invention has been particularly shown and described, it is apparent that various modifications may be made therein within the spirit and scope of the invention to attain useful pick-up of EKG signals transmitted to spaced panels of metallic cloth or textile material with metallic threads which are in contact compression with separate portions of the body of the subject to be monitored and which receive EKG signals through the body perspiration of the subject as the conductive medium, and that the invention is not limited to the particular shapes of components or specific materials described.

What is claimed is:

1. A flexible sensor pad for continuous biomedical monitoring of electrocardiogram signals from a clothed human subject through the clothing worn by the subject and without direct contact with the skin of the subject while the subject is being supported on a body-supporting surface portion of a subject supporting device and without attachment of electrical leads or sensors to the body or clothing of the subject, comprising a flexible backing sheet in the form of a thin flat panel of electrically non-conducting, non-corrosive, water-proof, flexible sheet material capable of conforming to the contour of a variety of shapes of the body-supporting surface portion and being of a size to span an area coextensive with a predetermined area of the subject's body, a pair of separate electrically conductive pick-up panels of highly conductive, non-corrosive flexible web-like material secured in overlying relation on said backing sheet in the form of two strip-like members physically and electrically spaced from each other in side-by-side relation located wholly within the periphery of said backing sheet to receive electrocardiogram signals from the subject by transmission to the pick-up panels through peripheral perspiration from the subject communicated through the clothing being worn by the subject, the pick-up panels being located to be in good compression pressure relation with a pair of spaced predetermined body areas of the subject, a thin flexible fabric cover of moisture-permeable textile material overlying the pair of pickup panels to be disposed in direct contact with clothing of the subject covering said predetermined body areas and isolated from direct contact with subject's skin in such body areas by said clothing and having sufficient open spaces therethrough to pass peripheral perspiration from the subject to the pick-up panels for transmission to the latter of the electrocardiogram signals, said fabric cover being secured peripherally to the backing sheet and completely covering said pick-up panels so that said pick-up panels are located wholly within the periphery of said fabric cover, and a pair of electrical signal conductors connected respectively in electrically conductive relation to the respective pick-up panels and extending beyond the backing sheet for connection to electrocardiogram signal processing circuitry.

2. A flexible sensor pad as defined in claim 1, wherein said electrically conductive pick-up panels are each a textile fabric panel formed predominantly of threads having some electrically conductive metallic strands.

3. A flexible sensor pad as defined in claim 1, wherein said electrically conductive pick-up panels are each a textile fabric panel formed predominantly of threads having some electrically conductive gold strands.

4. A flexible sensor pad as defined in claim 1, wherein said electrically conductive pick-up panels are each a textile fabric panel formed predominantly of threads having some electrically conductive metallic strands, the panels each being of generally rectangular configuration.

5. A flexible sensor pad as defined in claim 1, wherein said backing sheet is a flexible panel of water-proofed textile fabric.

6. A flexible sensor pad as defined in claim 2, wherein said backing sheet is a flexible panel of water-proofed textile fabric.

7. A flexible sensor pad as defined in claim 2, wherein said backing sheet is a flexible panel of water-proofed textile upholstery-type fabric.

8. A flexible sensor seat pad for continuous biomedical monitoring of electrocardiogram signals from a clothed human subject such as an aircraft pilot or the like being supported in seated position on the seat cushion portion of a chair-like device through the clothing worn by the subject without direct contact with the skin of the subject and without attachment of electrical leads or sensors to the body or clothing of the subject, comprising a flexible backing sheet in the form of a thin flat panel of electrically non-conducting, non-corrosive, water-proof, flexible sheet material capable of conforming to the contour of a variety of shapes of the upper surface of the seat cushion portion and being of a size to laterally span a major portion of the width of the buttocks portion of the subject's body, a pair of separate electrically conductive pick-up panels of highly conductive, non-corrosive flexible web-like material secured in overlying relation on said backing sheet in the form of two panel members physically and electrically spaced from each other in side-by-side relation located wholly within the periphery of said backing sheet at appropriate locations to respectively underly the respective buttocks of the subject in seated position on the chair-like device to receive electrocardiogram signals from the subject by transmission to the pick-up panels through peripheral perspiration from the subject communicated through the clothing being worn by the subject, a thin flexible fabric cover of moisture-permeable textile material overlying the pair of pick-up panels to be disposed in direct contact with clothing of the subject covering the subject's buttocks area and isolated from direct contact with the subject's skin by the subject's clothing and having sufficient open spaces therethrough to pass peripheral perspiration from the subject to the pick-up panels for transmission to the latter of the electrocardiogram signals, said fabric cover being secured peripherally to the backing sheet and completely covering said pick-up panels so that said pick-up panels are located wholly within the periphery of said fabric cover, and a pair of electrical signal conductors connected respectively in electrically conductive relation to the respective pick-up panels and extending beyond the backing sheet for connection to electrocardiogram signal processing circuitry.

9. A flexible sensor pad as defined in claim 8, wherein said electrically conductive pick-up panels are each a textile fabric panel formed predominantly of threads having some electrically conductive metallic strands.

10. A flexible sensor pad as defined in claim 9, wherein said backing sheet is a flexible panel of waterproofed textile fabric.

* * * * *